US006665560B2

(12) United States Patent
Becker et al.

(10) Patent No.: US 6,665,560 B2
(45) Date of Patent: Dec. 16, 2003

(54) SLEEP DISCONNECT SAFETY OVERRIDE FOR DIRECT HUMAN-COMPUTER NEURAL INTERFACES FOR THE CONTROL OF COMPUTER CONTROLLED FUNCTIONS

(75) Inventors: Craig Henry Becker, Austin, TX (US); Ira Richard Forman, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 245 days.

(21) Appl. No.: 09/971,219

(22) Filed: Oct. 4, 2001

(65) Prior Publication Data

US 2003/0069516 A1 Apr. 10, 2003

(51) Int. Cl.$^7$ ............................................. A61B 5/0476
(52) U.S. Cl. ..................................................... 600/544
(58) Field of Search ................................. 600/378, 544; 128/925

(56) References Cited

U.S. PATENT DOCUMENTS 4,883,067 A * 11/1989 Knispel et al. ............... 600/28
6,171,239 B1 * 1/2001 Humphrey .................. 600/372

FOREIGN PATENT DOCUMENTS

WO          WO 93/21615       * 10/1993       ......... A61B/5/0476

* cited by examiner

Primary Examiner—Carl Layno
(74) Attorney, Agent, or Firm—Jerry B. Kraft; Jeffrey S. LaBaw

(57) ABSTRACT

When a neural human-computer interface is used to control mechanical and electrical functions, the act of falling asleep by the user during neural control operations can produce undesirable and even disastrous results since neural activity would still be monitored and could produce involuntary signals leading to unintended results. In systems that track a user's neural activity and which use an electrical signal based upon this activity for controlling computer controlled functions, the problems associated with falling asleep may be circumvented by using an implementation which inhibits neural control when a patient's sleep state is detected. To accomplish this, an electroencephalography monitor (EEG) may be used to detect and predetermine the user's neural activity pattern during the transition from awake to sleep states. This pattern is compared against current neural activity. If matched, the neurally generated electrical signal is terminated.

24 Claims, 3 Drawing Sheets

SLEEP DISCONNECT SAFETY OVERRIDE FOR DIRECT HUMAN-COMPUTER NEURAL INTERFACES FOR THE CONTROL OF COMPUTER CONTROLLED FUNCTIONS

TECHNICAL FIELD

The present invention relates to direct Human-Computer neural interfaces, i.e. controlling of computers to perform various functions through human thought transmitted to computers as electrical signals.

BACKGROUND OF RELATED ART

Controlling computers with human thought, i.e brain waves, is no longer science fiction. Considerable work has been done with severely paralyzed persons who may not even have consistent head movement. Conventionally, the person's neural activity or brain waves may be monitored through the use of an electroencephalograph (EEG) which monitors the brain through an electrode cap mounted on the head.

Computers have already been controlled in a basic or rudimentary way through the measurement of the electrical activity of the human brain. The EEG records the voltage fluctuations of the brain which can be detected using electrodes attached to the scalp. The EEG signals arise from the cerebral cortex, a layer of highly convoluted neuronal tissue several centimeters thick. It is believed that the pyramidal cells of the cerebral cortex are the source of the EEG voltages. Each of these pyramidal nerve cells constitutes a tiny current dipole with a polarity that depends on whether the net input to the cell inhibits or excites. As a result, this dense layer of pyramidal cells produces a constantly shifting configuration of electrical activity as the nerve impulses change. The measurements on the scalp can detect the underlying electrical patterns in a form that is somewhat dulled by passage through the skull. For many years, researchers have tried to correlate the EEG signals with particular human behaviors and sensations. This work has resulted in a functional map of the human cerebral cortex. This map now enables experimenters to specifically tailor EEG experiments by placing electrodes on the parts of the scalp directly over the source of the activity to be monitored. In order to use this electrical activity to operate a computer, workers have tried to isolate specific EEG signals that people may be able to vary and adjust at will. Commonly, EEG signals are continuously monitored with unwanted components being filtered out.

In distinguishing wanted from unwanted components of these continuously monitored EEG signals, developers have categorized the waves by the frequency of their emanations: Alpha waves (8–13 Hz) that can be effected if the user concentrates on simple mentally isolated actions like closing one's eyes; Beta waves (14–30 Hz) associated with an alert state of mind; Theta waves (4–7 Hz) usually associated with the beginning of sleep or a "downer" mental state brought on by frustration or disappointment; and Delta waves (below 3.5 Hz) associated with deep sleep. Most attempts at computer control try to use the Alpha waves because users can learn to change the amplitude of Alpha waves by concentration, raising attention and isolation from other thoughts. Users have been enabled through the focusing and unfocusing of their attention to create EEG sensed Alpha waves sufficient to move and control a cursor on a computer screen. Once it becomes viable to, thus, control a computer, it also becomes viable to then use the computer to control various computer controlled mechanical and electronic functions.

Similar work is being done with neural activity from sources other than the brain. Electromyographic (EMG) sensors are attached to the person's skin to sense and translate muscular impulses to control computer functions. Patients have been reported to have moved objects on computer screens via EMG sensed tensing and untensing of facial muscles. Also Electrooculargraphic (EOG) signals have been sensed from eye movement and its use demonstrated to have moved items on a computer in a relatively rudimentary fashion.

The publication, *Controlling Computers with Neural Signals,* Hugh S. Lusted et al., Scientific American, October 1996 Issue, describes the above background material in greater detail. The authors are principals of Biocontrol Systems Inc., developers of systems in this technology.

While past use of neural signals to control computers has been primarily directed to the physically impaired, most of the research work is and will be applicable to control computers for other functions. For years, military developers have been exploring "no hands" computer control involving the sensing of neural signals. Such techniques are being developed for combat and other pilots.

An article, *Controlling Computers by Thought,* Toby Howard, published in Personal Computer World, February 1999, reports that tiny electrodes the size of a pen tip have been successfully implanted in people's brains in areas associated with specific neuromuscular activities. These electrodes called neurotropic electrodes need no internal wires for powering; they are powered by an induction coil worn in a user's cap. The signals from these electrodes are detected and amplified by a tiny receiver under the skull and transmitted to control a computer that the user learns to do via biofeedback. This device produces a signal that is an improvement over the EEG signals because unlike the EEG the signals are not muffled by passage through the skull.

SUMMARY OF THE PRESENT INVENTION

While direct neural interfaces between humans and computers for productive purposes outside of the physically impaired functions is in its infancy, it may be reasonably expected to increase in its applications. Since the neural human-computer interface is likely to be used to control mechanical and electrical functions, it should be understood that falling asleep by the user during neural control operations could produce undesirable and even disastrous results. During the sleep state, the neural activity would still continue to be monitored and produce involuntary signals leading to the unintended results.

Accordingly, the present invention seeks to circumvent the sleep problem by providing in a system for tracking neural activity in a user and using an electrical signal based on the tracked activity for controlling computer controlled functions, an implementation for preventing neural activity during said user's sleep from being used for controlling said functions. The present invention comprises the combination of means for predetermining a neural activity pattern indicative of the transition of a user from awake to asleep, means for monitoring the neural activity of the user for the predetermined neural activity pattern and means responsive to the detection of said predetermined neural activity pattern for terminating said use of said electrical signals. A convenient implementation for monitoring is through an EEG monitor. In one operative embodiment, the means for terminating should terminate use of electrical signals when said EEG monitor reading drops below 7 Hz, which is a conventional sleep threshold. However, it should be recognized that since sleep patterns will differ from person to person, the most accurate results may be achieved when the means for predetermining the neural activity pattern determines a specific signature pattern for each user based upon preliminary EEG testing on said user.

The present invention comprehends an implementation wherein means are provided proximate the user for the tracking of neural activity and there are means for transmitting the electrical signal to a computer remote from the user for controlling the computer controlled functions. In such an implementation, the means for transmitting said electrical signals are preferably wireless means.

BRIEF DESCRIPTION OF THE DRAWINGS

The present invention will be better understood and its numerous objects and advantages will become more apparent to those skilled in the art by reference to the following drawings, in conjunction with the accompanying specification, in which.

DETAILED DESCRIPTION OF THE PREFERRED EMBODIMENT

Figure 1:
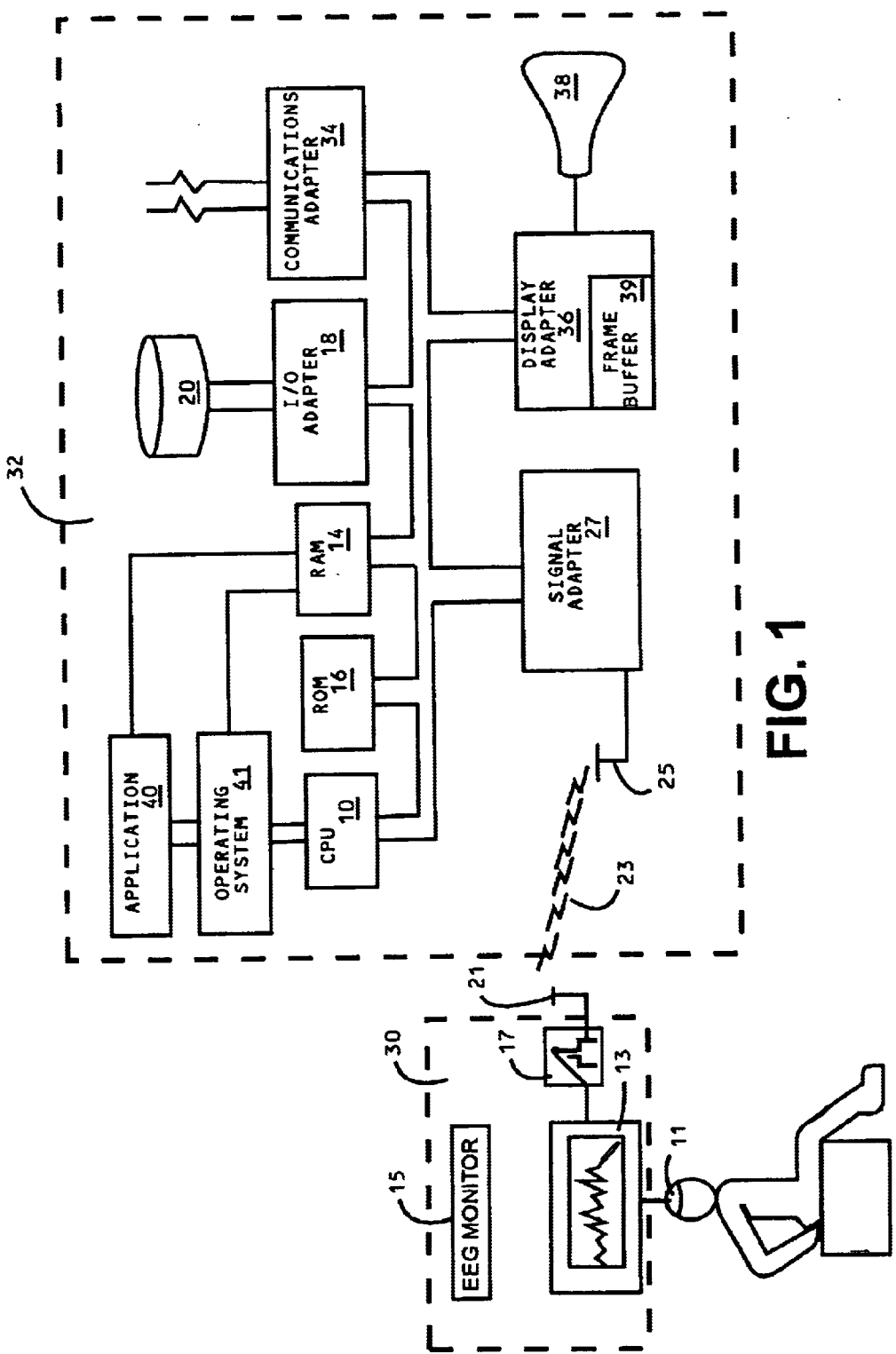
FIG. 1 is a block diagram of a data processing system including a central processing unit in which the neural activity of a user is monitored in accordance with the present invention and used to terminate when the user falls asleep in a system with a direct human-computer interface for the control of computer functions.

FIG. 1 is a diagram of an illustrative embodiment of the invention. The subject user 33 will use his neural activity to control items, such as icons or a cursor, on the display 38 of computer 32. A display interface provides the user with a visual feedback showing the application of neural activity to computer functions. However, a display is not required since the feedback to the user may be auditory. Also, the control may be of non-visual and non-auditory functions. Using the technology described hereinabove with respect to the *Controlling Computers with Neural Signals,* Hugh S. Lusted et al., Scientific American publication, electrode cap 11 on the skull of user 33 has a plurality of electrodes in contact with the scalp of the user. The neural activity is tracked on EEG apparatus 13. In this simple illustration, the neural activity tracked is EEG activity. In more sophisticated systems, EOG and EMG neural activity could also have been tracked. The electrical signals representative of the neural activity are transmitted 23 via antenna 21 to antenna 25 in computer 32 in a wireless setup. However, since user 33 is viewing display 38 to interactively control icons or cursors via biofeedback, the signals from tracking system 30 to computer 32 could have been directly wired instead of the wireless transmission 23.

To illustrate the present invention, the neural activity is monitored for an initial sleep pattern. This may be done simply by monitoring the EEG readings via monitor 15. Since the EEG readings are already being sensed by apparatus 13, the same EEG readings may be monitored. It is understood that the initiation of sleep is indicated by a Theta wave (3.5–7 Hz.) state for a period of more than a couple of seconds. Thus, monitor 15, upon sensing this sleep pattern, breaks the transmission 23, e.g. by opening switch 17. This switch 17 is just meant to be representational. There are many conventional ways to stop transmission 23. Actually, the signal may be transmitted to computer 32 and the application program 40 that will hereinafter be discussed in greater detail is notified of the transition to the sleep condition and then may terminate the use of the neural electrical signals from tracking system 30.

It should be noted that while a simple EEG monitoring using a set level may be sufficient to determine when the user passes into sleep, such an initial sleep transition may vary from user to user. In order to get greater accuracy, the sleep patterns of potential users may be monitored before the present system is used and the neural activity levels indicative of the transition from awake to asleep be predetermined for each specific user. Techniques for determining sleep transition neural activity levels and related technology are described in greater detail in the text, *Principles of Neuroscience,* edited by E. R. Kandel et al., 4th Edition, 2000, McGraw-Hill, New York, article by A. Rechtschaffen et al., *Sleep and Dreaming,* at pp. 936–947.

Also, the EEG monitoring may be combined with supplemental implementations to confirm that the user has passed from an awake to an asleep state. For example, considerable research has gone into the monitoring of and response to the user's facial expressions. Along these lines, in the present invention, the closure of user's eyes could be monitored with a still camera or a video camera. These implementations could be sampled in response to a monitored EEG signal that the user has passed into sleep in order to confirm that the user was asleep.

Computer 32 comprises signal adapter 27 which receives the neural signals from antenna 25 and connects to signal via computer bus 12 to central processing unit (CPU) 10, such as one of the PC microprocessors or workstations, e.g. eServer pSeries available from International Business Machines Corporation (IBM), which in turn is interconnected to various other components by system bus 12. An operating system 41 runs on CPU 10, provides control and is used to coordinate the function of the various components of FIG. 1. Operating system 41 may be one of the commercially available operating systems such as the AIX operating system available from IBM; Microsoft's WindowsMe™ or Windows 2000™, as well as various other UNIX and Linux operating systems. Application programs 40, controlled by the system, are moved into and out of the main memory Random Access Memory (RAM) 14. These programs include the programs for converting the received neural electrical signals into icon and cursor movements on the screen of display 38. The application programs may also include the present invention's monitoring the transition of the user from awake to asleep. A Read Only Memory (ROM) 16 is connected to CPU 10 via bus 12 and includes the Basic Input/Output System (BIOS) that controls the basic computer functions. RAM 14, I/O adapter 18 and communications adapter 34 are also interconnected to system bus 12. I/O adapter 18 may be a Small Computer System Interface (SCSI) adapter that communicates with the disk storage device 20 to provide the storage of a database. Communications adapter 34 interconnects bus 12 with an outside network. Display adapter 36 includes a frame buffer 39, which is a storage device that holds a representation of each pixel on the display screen 38. Images may be stored in frame buffer 39 for display on monitor 38 through various components, such as a digital to analog converter (not shown) and the like. By using the aforementioned I/O devices, a user is capable of inputting neural information to the system through signal adapter 27, i.e. signals to move icons or cursors and receiving output information from the system via display 38 showing the cursor movement.

Figure 2:
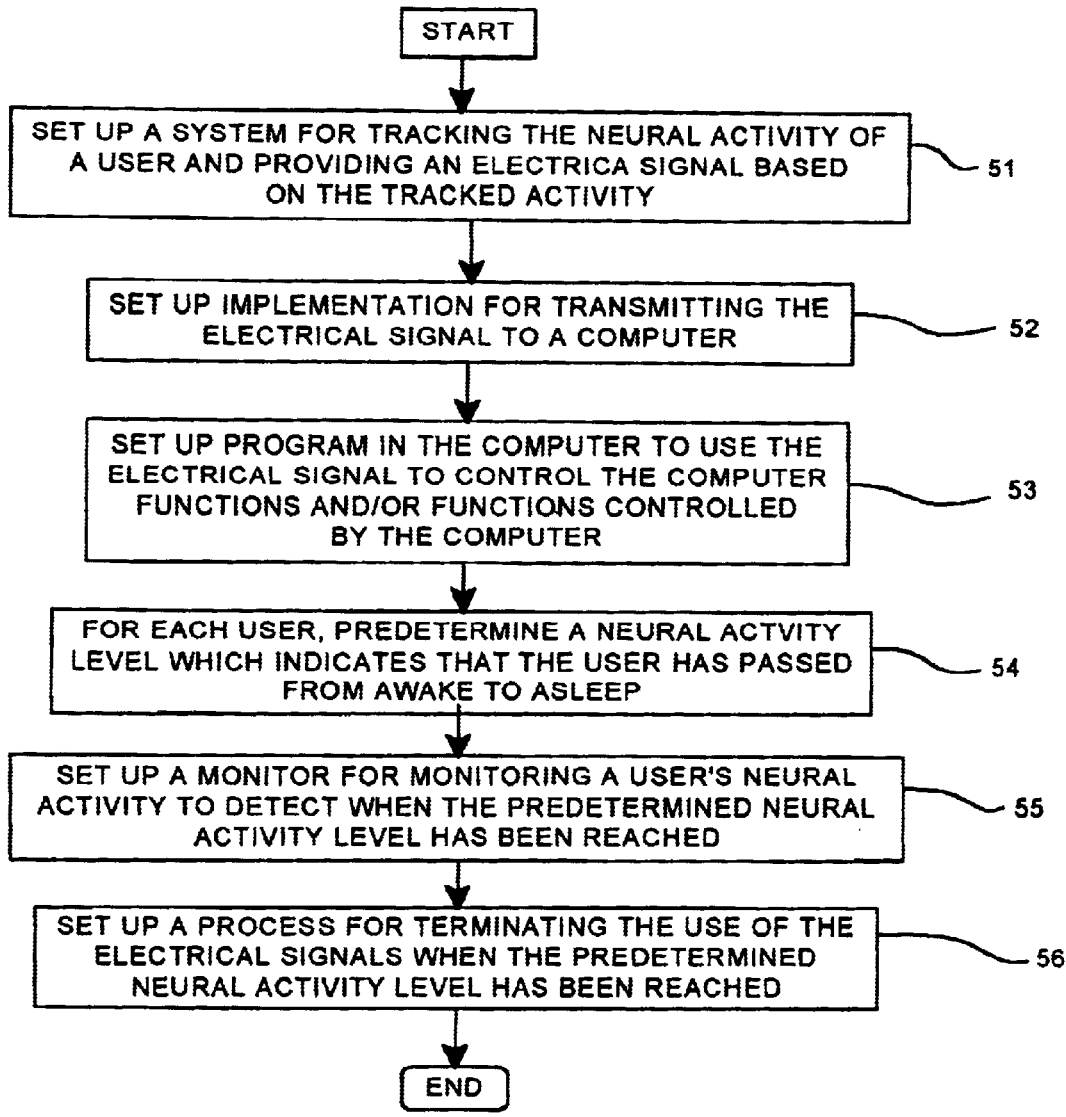
FIG. 2 is an illustrative flowchart describing the setting up of the process of the present invention for the monitoring of neural activity to determine when the user falls asleep in a system with a direct human-computer interface for the control of computer functions.

Now, with reference to FIG. 2, there will be described the setting up of a program according to the present invention for monitoring the sleep transition point of a user controlling a computer with sensed neural signals. A system is set up for tracking the neural activity of a user and providing an electrical signal based upon the activity, step 51. An implementation is also set up for transmitting the electrical signal to a computer, step 52. A program is set up in the computer to use the electrical signals to control computer functions and/or functions controlled by the computer, step 53. For each user, a process is provided for predetermining the neural activity level that indicates the user has passed from awake to asleep, step 54. There is set up a monitor for monitoring a user's neural activity to determine when the predetermined neural activity level of step 54 has been reached, step 55. Finally, a process is set up for terminating the use of the electrical signals to control the computer when the predetermined neural activity has been reached, step 56.

Figure 3:
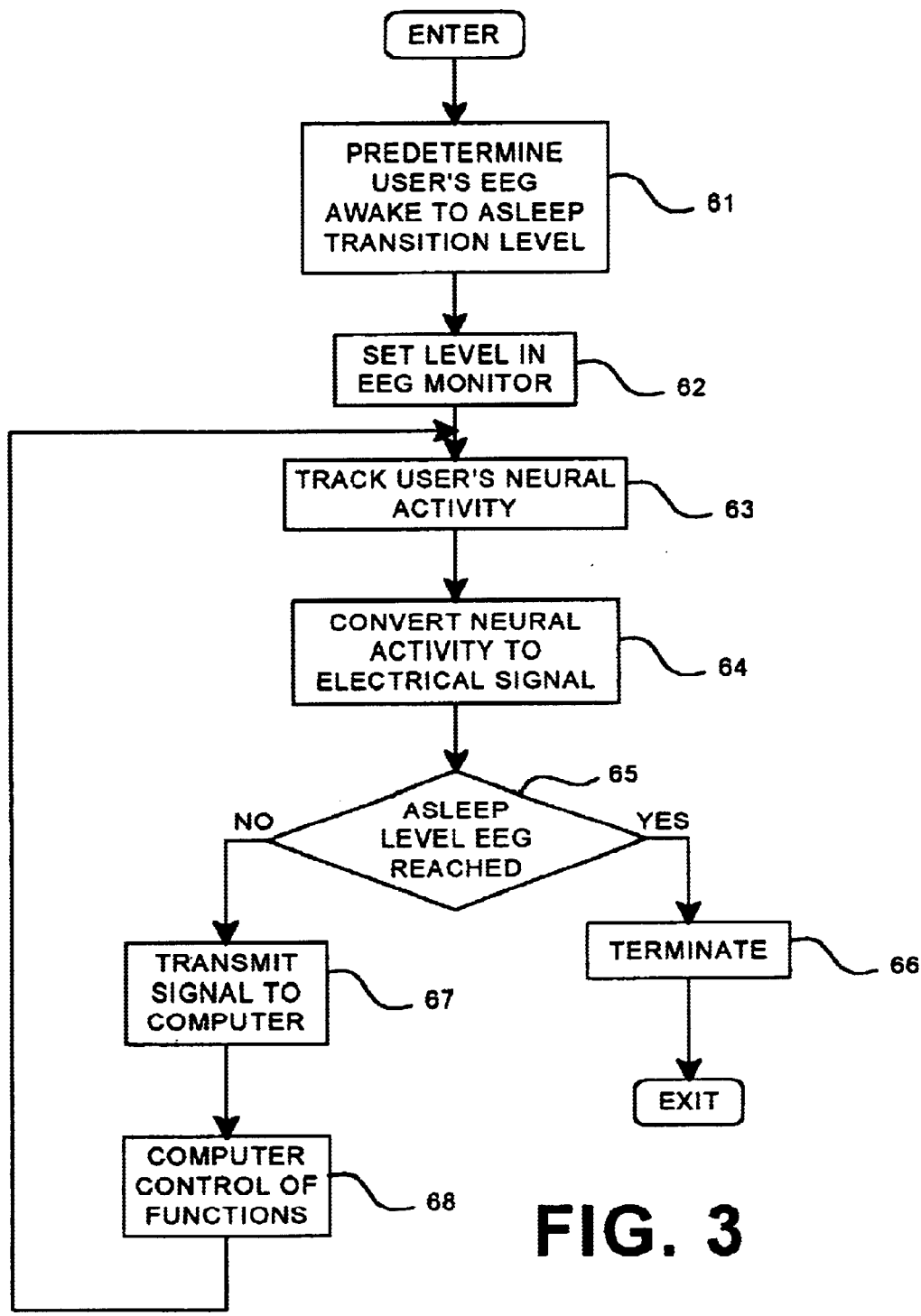
FIG. 3 is a flowchart of an illustrative run of the process setup in FIG. 2.

Now that the basic program set up has been described, there will be described with respect to FIG. 3 a flowchart of a simple operation showing how the program could be run. The user's awake to asleep transition EEG level is determined, step 61. The level is set in the EEG monitor, step 62. The user's neural activity is tracked, step 63, and converted to electrical signals, step 64, which are transmitted and used by the computer and the user interactively to control the computer or computer functions. A determination is made as to whether the awake to asleep EEG level has been reached, step 65. If No, the electrical signals are continued to be transmitted to the computer, step 67, and the user to control computer functions, step 68, while the user's neural activity continues to be tracked, step 63. If step 65 is Yes, the user's predetermined EEG level has been reached, the transmission is terminated and the session is exited.

While the primary implementation of the present invention is the monitoring of the awake to the asleep state of neural activity, the capability does exist for the monitoring of transitions of other neural defined states. These other defined states of neural activity may be representative of a patient's mental or emotional state (e.g. happy, disappointed, frustrated, etc.) with variations in neural activity occurring within states. It is likely that future applications for other computer controlled functions will be dependent on particular states of neural activity. In such situations, the present invention could be used in systems for varying the use of said electrical signals being used for controlling said functions in response to variations in the states of said neural activity comprising means for predetermining a neural activity pattern indicative of the transition of a user from one state of neural activity to another, means for monitoring the neural activity of said user for said predetermined neural activity pattern and means responsive to the detection of said predetermined neural activity pattern for changing said use of said electrical signals to control said computer controlled functions.

One of the preferred implementations of the present invention is in application program 40 made up of programming steps or instructions resident in RAM 14, FIG. 1. Until required by the computer system, the program instructions may be stored in another readable medium, e.g. in disk drive 20 or in a removable memory such as an optical disk for use in a CD ROM computer input or in a floppy disk for use in a floppy disk drive computer input. Further, the program instructions may be stored in the memory of another computer prior to use in the system of the present invention and transmitted over a LAN or a WAN, such as the Web itself, when required by the user of the present invention. One skilled in the art should appreciate that the processes controlling the present invention are capable of being distributed in the form of computer readable media of a variety of forms.

Although certain preferred embodiments have been shown and described, it will be understood that many changes and modifications may be made therein without departing from the scope and intent of the appended claims.

What is claimed is:

1. In a system for tracking neural activity in a user and using an electrical signal based on said tracked activity for controlling computer controlled functions, a system for preventing neural activity during said user's sleep from being used for controlling said functions comprising:
   means for predetermining a neural activity pattern indicative of the transition of a user from awake to asleep;
   means for monitoring the neural activity of said user for said predetermined neural activity pattern; and
   means responsive to the detection of said predetermined neural activity pattern for terminating said use of said electrical signals based on said tracked neural activity.

2. The system for tracking neural activity of claim 1 wherein said means for monitoring includes an electroencephalograph (EEG) monitor.

3. The system for tracking neural activity of claim 2 wherein said means for terminating terminate said use of electrical signals when said EEG monitor reading drops below 7 Hz.

4. The system for tracking neural activity of claim 2 wherein said means for predetermining said neural activity pattern determines a specific signature pattern for each user based upon preliminary EEG testing on said user.

5. The system for tracking neural activity of claim 1 including:
   means proximate said user for said tracking of neural activity; and
   means transmitting said electrical signal to a computer remote from said user for controlling said computer controlled functions.

6. The system for tracking neural activity of claim 5 wherein said means for transmitting said electrical signal are wireless means.

7. The system for tracking neural activity of claim 1 further including:
   means responsive to the detection of said predetermined neural activity pattern for monitoring a supplementary activity of said user for an indicator confirming that the user is asleep.

8. In a system for tracking neural activity in a user and using an electrical signal based on said tracked activity for controlling computer controlled functions, a method for preventing neural activity during said user's sleep from being used for controlling said functions comprising:
   predetermining a neural activity pattern indicative of the transition of a user from awake to asleep;
   monitoring the neural activity of said user for said predetermined neural activity pattern; and
   terminating said use of said electrical signals based upon said tracked neural activity responsive to the detection of said predetermined neural activity pattern.

9. The method of claim 8 wherein said step of monitoring neural activity includes the step of forming an electroencephalograph (EEG).

10. The method of claim 9 wherein said use of electrical signals is terminated when said EEG reading drops below 7 Hz.

11. The method of claim 9 wherein said step of predetermining said neural activity pattern determines a specific signature pattern for each user based upon preliminary EEG testing on said user.

12. The method of claim 8 including the steps of:

tracking said neural activity directly at the user; and transmitting said electrical signal to a computer remote from said user for controlling said computer controlled functions.

13. The system for tracking neural activity of claim 12 wherein said electrical signal is transmitted wirelessly.

14. The method of claim 8 further including the step of:

monitoring a supplementary activity of said user for an indicator confirming that the user is asleep responsive to the detection of said predetermined neural activity pattern.

15. A computer program having code recorded on a computer readable medium for preventing neural activity during a user's sleep from being used for controlling functions in a system for tracking neural activity in a user and using an electrical signal based on said tracked activity for controlling computer controlled functions, said computer program comprising:

means for predetermining a neural activity pattern indicative of the transition of a user from awake to asleep;

means for monitoring the neural activity of said user for said predetermined neural activity pattern; and means responsive to the detection of said predetermined neural activity pattern for terminating said use of said electrical signals based upon said tracked neural activity.

16. The computer program for tracking neural activity of claim 15 wherein said means for monitoring includes an electroencephalography (EEG) monitor.

17. The computer program for tracking neural activity of claim 16 wherein said means for terminating terminate said use of electrical signals when said EEG monitor reading drops below 7 Hz.

18. The computer program for tracking neural activity of claim 16 wherein said means for predetermining said neural activity pattern determines a specific signature pattern for each user based upon preliminary EEG testing on said user.

19. The computer program for tracking neural activity of claim 15 including:

means proximate said user for said tracking of neural activity; and means transmitting said electrical signal to a computer remote from said user for controlling said computer controlled functions.

20. The computer program for tracking neural activity of claim 19 wherein said means for transmitting said electrical signal are wireless means.

21. The computer program for tracking neural activity of claim 15 further including:

means responsive to the detection of said predetermined neural activity pattern for monitoring a supplementary activity of said user for an indicator confirming that the user is asleep.

22. In a system for tracking neural activity in a user and using an electrical signal based on said tracked activity for controlling computer controlled functions, a system for varying the use of said electrical signals being used for controlling said functions in response to changes in defined states of neural activity comprising:

means for predetermining a neural activity pattern indicative of the transition of a user from one defined state of neural activity to another defined state;

means for monitoring the neural activity of said user for said predetermined neural activity pattern; and means responsive to the detection of said predetermined neural activity pattern for changing said use of said electrical signals to control said computer controlled functions to a use consistent with the defined state.

23. In a system for tracking neural activity in a user and using an electrical signal based on said tracked activity for controlling computer controlled functions, a method for varying the use of said electrical signals being used for controlling said functions in response to variations in the states of said neural activity comprising:

predetermining a neural activity pattern indicative of the transition of a user from one defined state of neural activity to another defined state;

monitoring the neural activity of said user for said predetermined neural activity pattern; and changing said use of said electrical signal to control said computer controlled functions to a use consistent with the defined state responsive to the detection of said predetermined neural activity pattern.

24. In a system for tracking neural activity in a user and using an electrical signal based on said tracked activity for controlling computer controlled functions, a computer program having code recorded on a computer readable medium for varying the use of said electrical signals being used for controlling said functions in response to changes in defined states of neural activity comprising:

means for predetermining a neural activity pattern indicative of the transition of a user from one defined state of neural activity to another defined state;

means for monitoring the neural activity of said user for said predetermined neural activity pattern; and means responsive to the detection of said predetermined neural activity pattern for changing said use of said electrical signals to control said computer controlled functions to a use consistent with the defined state.

* * * * *